(12) United States Patent
Bendett et al.

(10) Patent No.: US 7,131,968 B2
(45) Date of Patent: Nov. 7, 2006

(54) APPARATUS AND METHOD FOR OPTHALMOLOGIC SURGICAL PROCEDURES USING A FEMTOSECOND FIBER LASER

(75) Inventors: Mark Bendett, Ann Arbor, MI (US); Mark Bischoff, Elleben OT Reichheim (DE); Mario Gerlach, Eisenberg (DE); Dirk Muehlhoff, Kunitz (DE)

(73) Assignees: Carl Zeiss Meditec AG, Jena (DE); IMRA America, Inc., Ann Arbor, MI (US)

( * ) Notice: Subject to any disclaimer, the term of this patent is extended or adjusted under 35 U.S.C. 154(b) by 187 days.

(21) Appl. No.: 10/625,797

(22) Filed: Jul. 23, 2003

(65) Prior Publication Data

US 2004/0243112 A1 Dec. 2, 2004

Related U.S. Application Data

(60) Provisional application No. 60/475,583, filed on Jun. 2, 2003.

(51) Int. Cl.
*A61B 18/18* (2006.01)
*A61B 18/22* (2006.01)

(52) U.S. Cl. .............................. 606/10; 606/4; 606/17; 372/25; 359/333

(58) Field of Classification Search .............. 606/3–13, 606/16–18; 372/25; 385/4, 5; 359/326, 359/333
See application file for complete search history.

(56) References Cited

U.S. PATENT DOCUMENTS

| | | | | |
|---|---|---|---|---|
| 5,656,186 A | * | 8/1997 | Mourou et al. | 219/121.69 |
| 5,696,782 A | * | 12/1997 | Harter et al. | 372/25 |
| 5,815,307 A | * | 9/1998 | Arbore et al. | 359/328 |
| 6,195,369 B1 | * | 2/2001 | Kumar et al. | 372/26 |
| 6,249,630 B1 | * | 6/2001 | Stock et al. | 385/123 |
| 6,272,156 B1 | * | 8/2001 | Reed et al. | 372/25 |
| 6,872,202 B1 | * | 3/2005 | Gerlach et al. | 606/10 |

* cited by examiner

*Primary Examiner*—A. Farah
(74) *Attorney, Agent, or Firm*—Reed Smith LLP (57) ABSTRACT

Apparatus and method to generate a stream of pulses having a pulse repetition rate of at least about 50000 pulses per second and a per-pulse length of less than one picosecond, and to scan and focus the stream to an output light pattern suitable to sculpt tissue for a surgical procedure (e.g., ophthalmologic) using at least a high number of pulses to complete the operation in a matter of a few second, e.g., 100000 pulses in less than ten seconds. A laser having a optical fiber gain medium generates a stream of femtosecond pulses. Some embodiments create a preconditioning negative dispersion that compensates for positive dispersion in the scanning system. In some embodiments, a lenticule is cut using the laser and scanning system and is mechanically removed through a side slit formed through the cornea surface.

36 Claims, 4 Drawing Sheets

APPARATUS AND METHOD FOR OPTHALMOLOGIC SURGICAL PROCEDURES USING A FEMTOSECOND FIBER LASER

RELATED APPLICATION

This claims priority to U.S. Provisional Patent Application No. 60/475,583 filed Jun. 2, 2003 entitled APPARATUS AND METHOD FOR OPHTHALMOLOGIC SURGICAL PROCEDURES USING A FEMTOSECOND FIBER LASER, which is incorporated in its entirety by reference.

FIELD OF THE INVENTION

This invention relates to the field of surgical laser tools, and more specifically to a method and apparatus for ophthalmologic surgical procedures using a femtosecond fiber laser.

BACKGROUND OF THE INVENTION

Laser-based apparatus for refraction-correction ophthalmologic surgery, such as the LASIK (laser in situ keratomileusis) procedure, can correct various vision impairments such as myopia (i.e., near-sightedness), hyperopia (i.e., farsightedness) and astigmatism by surgically reshaping the cornea of the eye. Hyperopia is measured in terms of positive diopters. Myopia is measured in terms of negative diopters. The most common refractive errors ranged between +6 to −6 diopters. For example, if part of the corneal stroma (the interior bulk of the cornea) is removed, the created void can be made to close. The result is a reshaped cornea.

Conventionally, LASIK procedures use a mechanical knife, called a keratome, to create a flap, The mechanical flap-creation procedure can damage the cornea and stroma tissue, possibly requiring an extended healing period and leaving undesirable artifacts such as haze, scarring, and/or instability of the correction, which interfere with vision in some cases.

Further, once the flap is created and folded back, conventional LASIK procedures typically use a high-powered ultraviolet excimer laser to photoablate a pattern (e.g. of spots) to reshape the stroma. Such a process is relatively crude, due to the relatively large size of the spots and possibly due to heating and acoustic shockwaves from the excimer photoablation. That is, the relatively course granularity of the excimer laser procedure and its higher energy pulses leaves something to be desired. After shaping the stroma, the flap is repositioned to complete the surgery.

As described in U.S. Pat. No. 6,110,166 issued Aug. 29, 2000 entitled "Method for corneal laser surgery" (and incorporated herein by reference), a LASIK-type surgery procedure can be made more effective and efficient if the flap that is created can be repositioned in an interlocking relationship with the undisturbed corneal tissue. A flap with an interlockable configuration can be created. The flap could then be lifted to expose the corneal tissue that is to be removed and, next, after the desired amount of corneal tissue is removed, the flap could be repositioned and interlocked with undisturbed corneal tissue to hold the flap in place during the healing process. The use of laser systems for ophthalmic surgical procedures, such as for other procedures contemplated for the present invention, is particularly appropriate due to the extreme precision required when corneal tissue is to be removed. Depending on the diameter and the general shape of the tissue volume to be removed, the removal of a layer of stromal tissue that is only approximately ten microns thick can result in a one diopter change. The removal of a lens shaped volume of tissue that is four millimeters in diameter and approximately fifty microns thick at its center can result in a active correction of approximately four diopters Thus, for vision corrections to achieve accuracy within one-diopter, the surgical procedure employed must be capable of precisely removing corneal tissue having a thickness which is accurate to within less than ten microns. Further, this degree of accuracy applies for any refractive correction regardless of the total amount of correction required.

The correction of myopia requires removal of a volume of conical tissue having a different shape than does the correction of hyperopia. Also, the limits of potential correction are different. For a myopic correction, a lentoid or lens-shaped volume of stromal tissue is removed. At the present time, myopic corrections of up to approximately thirty diopters can be reasonably expected. On the other hand, corrections of hyperopic conditions can be made up to only about fifteen diopters. Furthermore, for a hyperopic correction the volume of stromal tissue that is removed is thicker towards the edges than in the center.

Conventional femtosecond laser apparatus for eye surgery takes a relatively long time to form the cuts, typically in the order of one minute, during which time the eye must be held in a fixed position in order that the cuts are contiguous and formed in the shape that was predefined.

There is thus a need for an improved apparatus for fast refraction-correction ophthalmologic surgery in order to change the corneal curvature in a controlled way without affecting the corneal clarity or the integrity of the various membranes surrounding the stroma.

SUMMARY OF THE INVENTION

The present invention provides a high-repetition rate femtosecond laser coupled to a high-speed scanner, which results in a finer granularity in forming cuts in the stroma of the eye, and a much shorter duration of the surgical procedure, thus reducing the chance that the eye could move during the operation.

In some embodiments, the individual spots are created in a pattern wherein temporally sequential pulses are in a spaced-apart configuration in the stroma, in order to reduce the cumulative heating of and/or shock to local areas. For example, most or all spots can be formed wherein temporally adjacent pulses are used to create spots having a spacing at least two times the spot-to-spot spacing of spots in the array.

DESCRIPTION OF PREFERRED EMBODIMENTS

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

The use of femtosecond laser pulses allows the laser-induced optical breakdown (LIOB) spot size to be drastically reduced, and thus a smoother shape can be obtained. (See Juhasz et al. "CORNEAL REFRACTIVE SURGERY WITH FEMTOSECOND LASERS," IEEE Journal of Selected Topics in Quantum Electronics, Vol. 5, No. 4 July/August 1999, which is incorporated herein by reference.) The tissue effects are achieved by plasma formation that results from applying a sufficient fluence (energy/area) to reach a threshold, and thus destroy tissue in the focal volume. This creates a very small cavitation bubble, however a large number of such spots next to one another can form a quite-precise plane or curved surface. In fat, the traditional keratome knife can be replaced by using an array of closely spaced LIOB spots to create a cut, and a smoother surface can be achieved using sufficiently small focused laser spots in a well-controlled pattern However, a larger number of laser pulses are required to cover a given area with spots having the smaller spot size.

Nanosecond lasers require a relatively large energy (on the order of one or more milliJoules per pulse) to achieve threshold fluence for photodisruption. The large energy then causes undesirable secondary effects such as heating, large cavitation bubbles and/or shockwaves to the surrounding tissues. Decreasing the pulse duration to the femtosecond range significantly reduces threshold fluence, and also significantly reduces shockwave damage and heating.

With conventional ophthalmologic machines, femtosecond pulsed lasers operating in the range of 5000 pulses per second are used and a field of 100,000 to 300,000 or more pulses can be needed to effect each ophthalmologic cut. It can take up to a minute or more to complete a laser-based cut or series of cuts using these slow pulse rates. Some way is therefore required to hold the eye motionless for that approximately minute-long procedure. For that purpose, various techniques and procedures have been devised, such as holding the eyeball with a suction-activated ring fined circumferentially around the edge of the cornea for the duration of the operation. Even so, some researchers have reported experiencing loss of immobilization in up to two percent of the eyes operated on. Such complications can result in having to undergo multiple operations, or possibly in loss of vision due to cutting the wrong area of the eye.

U.S. Pat. No. 6,552,301 issued Apr. 22, 2003 to Herman et al. entitled "Burst-Ultrafast Laser Machining Method," describes combining ultrafast laser pulses and high-repetition rate (>100 KHz) bursts or continuous operation to control thermal and/or other relaxation processes between each laser pulse to ablate a sample surface. I.e., by repeating many pulses in a small area, the surface is not allowed to cool between pulses and heats due to accumulated fluence (up to 31 $J/cm^2$ or even 1000 or more $J/cm^2$, but limited to a very small spot). That is, a subsequent pulse is directed to the same spot as the prior pulse as soon as the plasma-plume expansion dissipates, in order that the beat from the first pulse does not dissipate before the subsequent pulse arrives. In contrast, some embodiments of the present invention provide for moving the target location of a subsequent second pulse to some predetermined distance away from the spot of its immediately prior first pulse, in order that heat does not accumulate, thus avoiding heat damage to surrounding tissue. At a later time (after any heat has dissipated somewhat from the first and second pulses), the intermediate locations between the first and second spot will be targeted. Further, one or more fields (i.e., surfaces each having a length, width, and height pattern of spots) can be scanned in a very short time with a series of laser-pulse spots to form one or more cuts in the stroma and/or cornea of the eye, or cuts of other tissues in a living animal such as a human. Because the entire series of cuts is performed in a very short time period, there is less movement, or likelihood of movement, of the subject's eye, thus reducing the chance of an erroneous cut.

Figure 1:
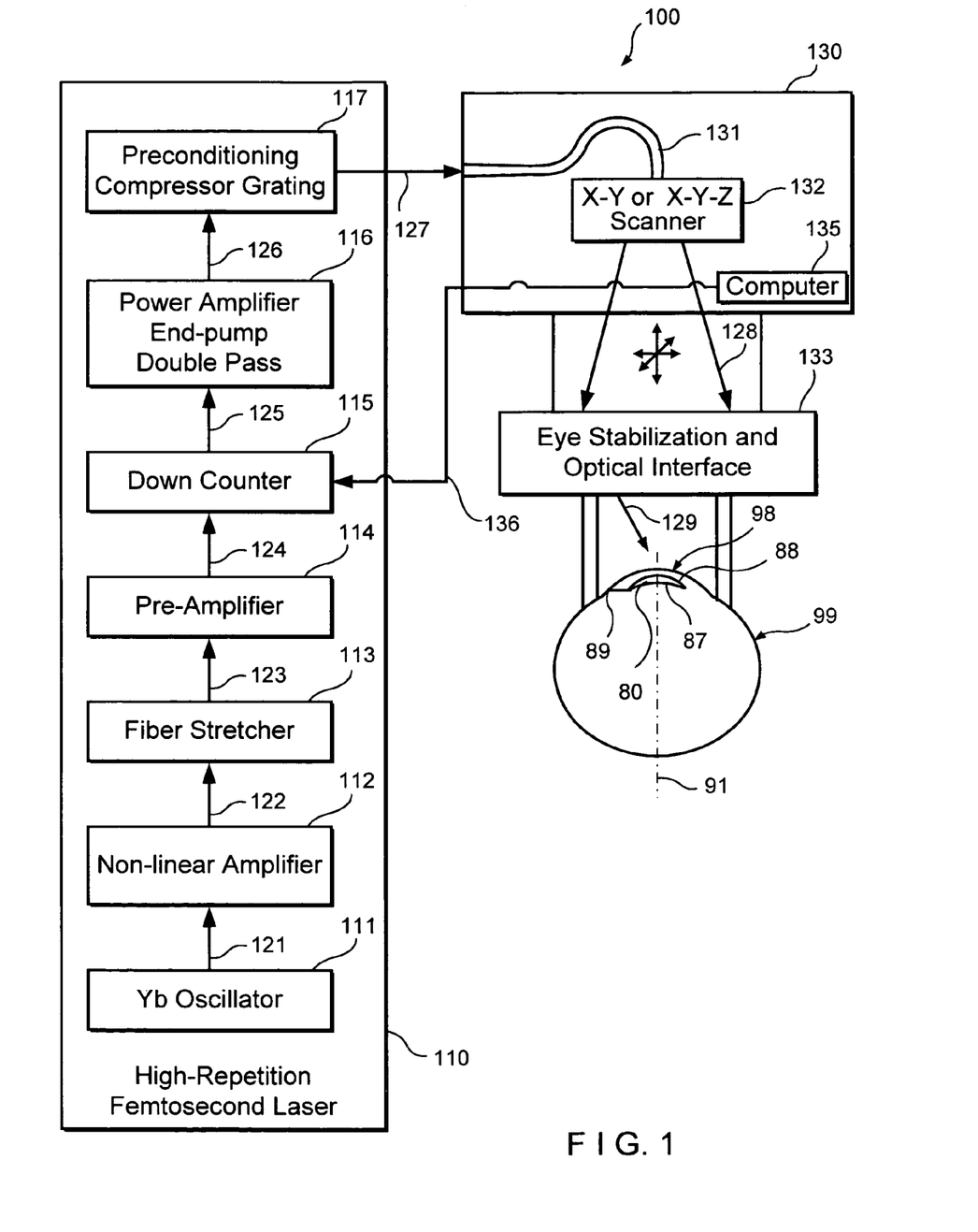
FIG. 1 shows a schematic view of an apparatus 100 according to one embodiment of the present invention.

FIG. 1 shows a schematic view of an apparatus 100 according to one embodiment of the present invention. Apparatus 100 includes a laser system 110 and a scanner system 130. Laser system 110 produces outputted laser pulses at a high repetition rate (e.g. from 50,000 to 1,000,000 pulses per second or more are output, although a much higher rate of pulses is originally generated internally in some embodiments). The pulses have a pulse shape and dispersion preconditioning such that once passed through scanning system 130, the light will produce femtosecond pulses (i.e., as used herein, these are pulses each having a duration of less than one picosecond, meaning pulses between about one femtosecond and about 999 femtoseconds). In some embodiments, each pulse is focused to a very small volume (e.g., about 1 micron by 1 micron by 1 micron, in some embodiments) to cause a femtosecond photodisruption event. By choosing a short pulse duration (e.g., in some embodiments, a 350-femtosecond duration) and small focal size (e.g., 5 microns or less), a very precise surface can be formed by an array of photodisruption-volume spots (herein called "spots"). In some embodiments, the energy of each pulse as it leaves laser system 110 is about two microJoules, and after passing through scanning system 130, is about one microJoule as it reaches the eye 99.

Apparatus 100 generates a scanned pulsed laser beam 129 directed onto an eye 99 of a patient in some embodiments, laser section 110 includes one or more sections that have a fiber optical gain medium used to initially create the stream of very short optical pulses, or to amplify the pulses, or to condition, select (i.e., allow some pulses to go through and eliminate other pulses), and/or shape the temporal and/or spatial characteristics of the pulses. The fiber optic gain sections are typically pumped with optical energy having a shorter wavelength than the wavelength of the laser light, in order to create an inverted population of lasing species. In some embodiments, the laser section 110 is capable of generating a pulsed laser beam 127 having physical characteristics similar to those of the laser beams generated by a laser system as disclosed and claimed in U.S. Pat. No. 6,249,630 (incorporated here by reference), which is also assigned to the assignee of the present invention. Furthermore, the present invention contemplates the use of a scanned pulsed laser beam 129 which has pulses with durations as long as a few picoseconds or as short as only a few femtoseconds.

Figure 10:
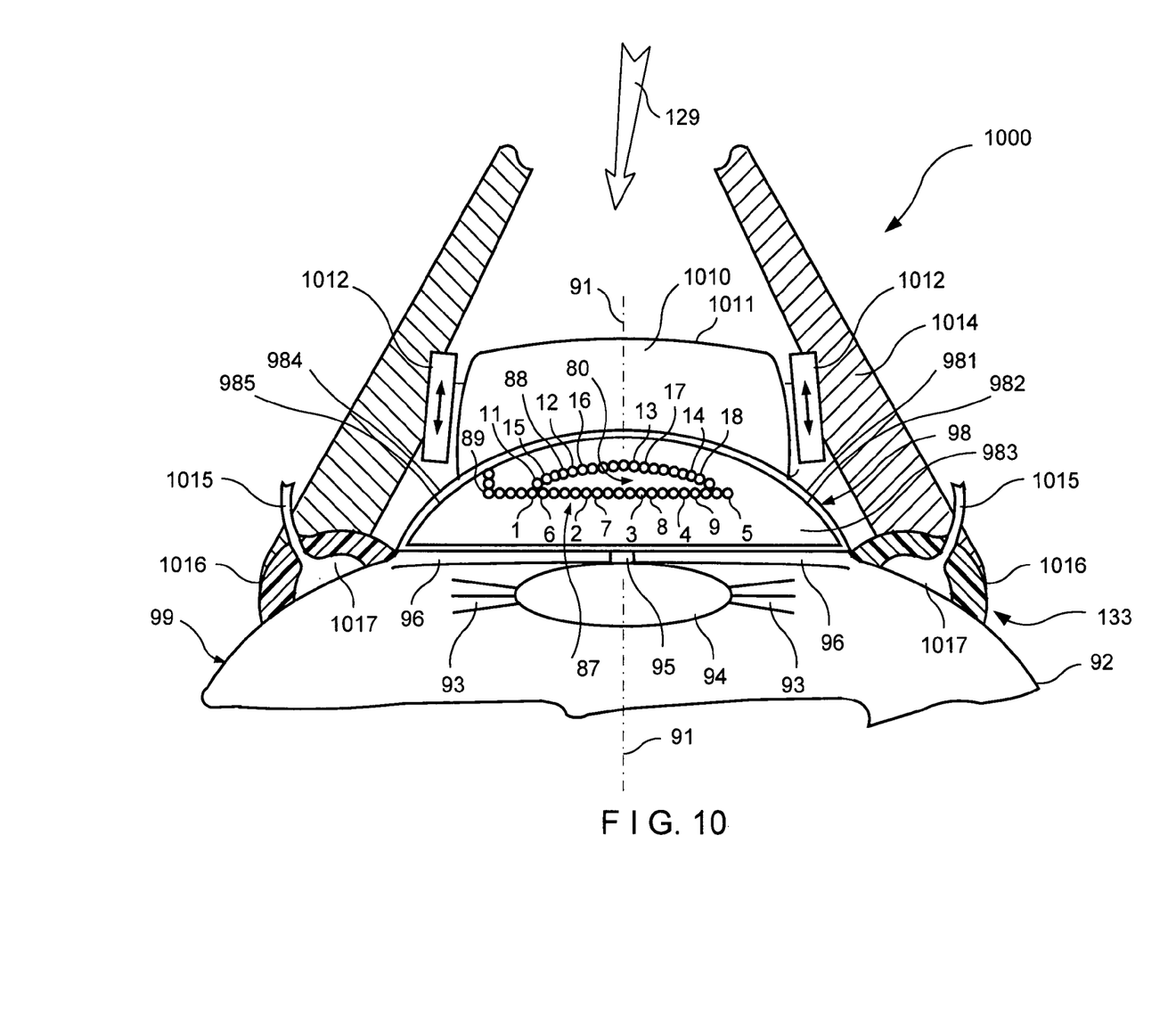
FIG. 10 is a side cross-section view of the eye 99 of FIG. 1, showing more details.

As shown in more detail in FIG. 10, the anatomical structure of eye 99 includes cornea 98 anterior to the pupil 95, the iris 96, and the sclera 92. Optical axis 91 of eye 99 passes through the cornea 98. The tissue of cornea 98 is transparent to visible and near-infrared light Going in a direction from top (anterior of cornea 98) to bottom (posterior of cornea 98) in FIG. 10, the tissue layers of cornea include the epithelium 981, Bowman's membrane 982 (5–10 microns thick), stroma 983, Decemet's membrane 984 (5 microns thick), and endothelium 985. In some embodiments, the stroma 983 is most important for the present invention, as it contains the only tissue that is removed for correction of the patient's vision.

As indicated above, the correction for myopia, hyperopia, and/or astigmatism can be accomplished by the removal of a predetermined volume of stromal tissue, The particular volume and shape of stromal tissue to be removed for the correction of myopia depends on the type and amount of correction required. To correct myopia, a lens-shaped (lentoid) volume is removed. Such a lentoid volume 80 is shown in cross-section in FIGS. 1 and 10. The lentoid volume 80 is defined by an anterior surface 88 and a posterior surface 87. Together, the anterior surface 88 and the posterior surface 87 completely enclose and separate the lentoid volume 80 of stromal tissue 983 that is to be removed from the rest of the stroma. To obtain the lens shape of the lentoid volume 80 for myopic correction, anterior surface 88 may be convex in shape and the posterior surface 87 may be planar, convex, or concave in shape.

In some embodiments, a corneal-aplanation device such as described in U.S. Pat. No. 6,254,595 issued Jul. 3, 2001 (and incorporated herein by reference) is used to aplanate (flatten) the anterior surface of tie cornea for at least a portion of the surgical procedure, in order to reduce coma and/or spherical aberration of the focused laser spot. Further, this allows the anterior surface 88 to be cut as parallel to the flat contact surface of the aplanating lens, and then the cornea and the anterior surface 88 will restore to a curved shaped when the aplanating lens is removed. This is useful for making a flap for LASIK procedures, but would require a custom-made curved contact lens (rather than other contact lens) to make a cut that is not conforming to a surface equidistant to the cornea surface when completed.

In other embodiments, a curved contact lens 1010, such as shown in FIG. 10, is used instead of a planar contact lens, in order to reduce excess pressure on the cornea, which can cause undesirable secondary effects like glaucoma in these embodiments, the scanner optics precompensates for the combined optical effects of contact lens 1010 and cornea 98 to reduce or eliminate coma and spherical aberration. Further, three-dimensional shapes can be cut, allowing much better correction of astigmatism, and a better corneal surface shape of the final result. Note that as a laser pulse is shortened, its bandwidth (i.e., range of colors) increases, and the optics of scanner system 130, in some embodiments, is corrected for spherical aberration that would otherwise smear the focus of the light, with some colors focused too near and other colors focused too far.

In some embodiments, a cleaning device such as described in U.S. Pat. No. 6,344,040 issue Feb. 5, 2002 (and incorporated herein by reference) is used to aspirate resulting gas and debris from the surgical procedure In other embodiments, a saline flush is directed, for example, either freehand or from tubing attached to the frame of scanning system 130.

In some embodiments, a laser system 110 is built according to the teaching of U.S. Pat. No. 6,249,630 (incorporated herein by reference) by Stock et al, issued Jun. 19, 2001 and assigned to an assignee of the present invention.

Referring to FIG. 1, in some embodiments, a Yb oscillator 111 such as a passively modelocked fiber laser, generates a series of optical pulses (a pulse steam) 121. In some embodiments, the pulses of optical pulse stream 121 have a wavelength of 1050 nm, a bandwidth of 2.5 nm, a pulse length of 1.5 ps, a power of 10 mW, a pulse rate of 50 MHz (i.e., 50,000,000 pulses per second), and a per-pulse energy of 0.2 nJ. Since the wavelength centered at 1050 nm in these embodiments is in the infrared (visible light being about 400 nm (blue-violet) to 700 nm (deep red)), there is less chance of startling the patient or causing stress and discomfort during the procedure than if visible light were used.

In some embodiments, pulse stream 121 is amplified by non-linear fiber amplifier 112 to generate pulse stream 122, which has a wavelength of 1050 nm, a bandwidth of 20 nm, a pulse length of 1.5 ps, a power of 60 mW, a pulse rate of 50 MHz (i.e., 50,000,000 pulses per second), and a per-pulse energy of 1.2 nJ.

I.e., pulse strewn 122 is conditioned by fiber pulse stretcher 113 to generate pulse stream 123, which has a wavelength of 1050 nm, a bandwidth of 20 nm, a pulse length of 200 ps, a power of 1 mW, and a pulse rate of 50 MHz (i.e., 50,000,000 pulses per second).

In some embodiments, pulse strewn 123 is amplified by fiber pre amplifier 114 to generate pulse stream 124, which has a wavelength of 1050 nm, a bandwidth of 15 nm, a pulse length of 150 ps, a power of 500 mW, a pulse rate of 50 MHz (i.e., 50,000,000 pulses per second), and a per-pulse energy of 10 nJ.

In some embodiments, pulse stream 124 is decimated (i.e., all but selected pulses are removed) by downcounter 115 (e.g., in some embodiments, an acousto-optic modulator) to generate pulse stream 125, which has a wavelength of 1050 nm, a bandwidth of 15 nm, a pulse length of 150 ps, a power of 0.7 mW, and a pulse rate of 200 KHz (i.e., 200,000 pulses per second).

In some embodiments, pulse stream 125 is amplified by fiber power amplifier 116 to generate pulse stream 126, which has a wavelength of 1050 nm, a bandwidth of 10 nm, a pulse length of 100 ps, a power of 800 mW, and a pulse rate of 200 KHz (i.e., 200,000 pulses per second).

In some embodiments, pulse stream 126 is pre-conditioned by grating compressor 117 to generate pulse stream 127, which has a wavelength of 1050 nm, a bandwidth of 10 nm, a pulse length of 350 fs, a power of 400 mW, a pulse rate of 200 KHz (i.e., 200,000 pulses per second), and a per-pulse energy of 2.0 microJoules. Grating compressor 117 not only recompresses the pulse stretching from fiber pulse stretcher 113 and the other optics internal to laser system 110, but also precompresses (provides dispersion that is the same magnitude and opposite sign) for the dispersion of the optical path through scanner system 130.

In some embodiments, scanner system 130 and laser system 110 are packaged as a single integrated t as viewed from the outside.

In some embodiments, scanner system 130 includes an input optical path 131 (such as an optical fiber) and an X-Y (two dimensional) or X-Y-Z (three-dimensional) scanner 132 controlled by computer 135 to generate 3D scan pattern 128 that, when passed through the optical interface portion of eye-stabilization and optical interface 133, creates the desired pattern of spots. Scanner 132 also includes compensation optics tat, when combined with the optical path inside scanner 132 and the optical path in eye-stabilization and optical interface 133, forms well-focused spots within the stroma of cornea 98.

In some embodiments, galvanometer scanners are used in scanner 132 to deflect the laser beam in the X- and Y-directions, and in some embodiments, the Z-direction scanning (focus-depth displacement scanning) is controlled by displacement of a displaceable collimator lens, as described in U.S. Pat. No. 6,356,088 issued Mar. 12, 2002, and in U.S. Pat. No. 6,167,173 issued Dec. 26, 2000, which are each incorporated by reference.

In some embodiments, scanner system 130 also includes a refraction-measuring system (such as described in U.S. Pat. No. 6,325,513 issued Dec. 4, 2001, in U.S. Pat. No. 6,149,272 issued Nov. 21, 2000, and in U.S. Pat. No. 6,515,739 issued Feb. 4, 2003, which are each incorporated by reference) to measure the needed amount, type, and spatial distribution of refractive correction needed. The computer 135 then controls scanner 132 to provide the cuts that will achieve the needed correction derived from the measurement.

In some embodiments, computer 135 also outputs control signal 136 that controls the timing of each pulse. E.g., if and when a slightly longer time is needed to move the scaring mechanics of scanner 132, the corresponding pulse can be delayed by control signal 136 to the desired time.

In some embodiments, a procedure, called herein femtosecond lamellar keratoplasty (FLK) is performed. FLK uses an array of individual photodisruption spots to define a lens-shaped block of tissue (a "lenticule") that is removed from the stroma through a side incision or from the surface of stroma exposed by a folded-back flap. A conventional procedure wing a microkeratome is referred to as "automated lamellar keratoplasty," or ALK The precision and flexibility associated with femtosecond photodisruption allows FLK to compete favorably and directly with LASIK. Many variations on this procedure are possible. A first cut 87 (planar, convex or concave) is made inside the cornea, defining the lenticule posterior surface. A second cut 88 (usually convex) is made defining the lenticule anterior surface. This cut may be extended to form a slit 89, or extended circumferentially further to form a flap to allow fuller access. Through the slit, or after the flap is lifted, the lenticule is then removed with hand instruments. Then the flap is replaced to form the new cornea shape, resulting in a direct refractive correction.

Figure 2:
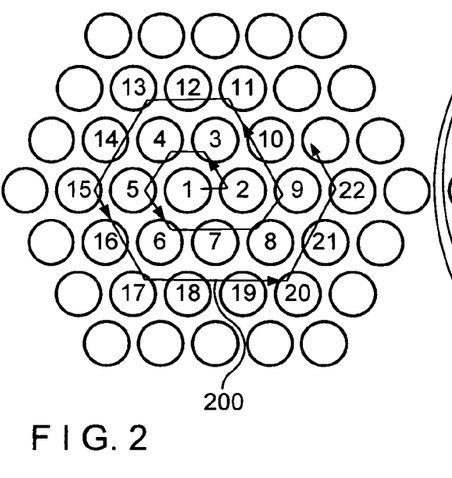
FIG. 2 is a plan view of a scan pattern 200 for an array of spots.

FIG. 2 is a plan view of a scan pattern 200 for an array of spots according to some embodiments of the invention. In the embodiment shown, adjacent scan pattern 200 forms a spiral, wherein each temporally successive laser pulse forms a spot that adjoins the just previous spot. Reference numbers 1 through 22 represent the temporal order in which the spots are formed. Other similar embodiments use a Cartesian scan pattern (where each successive X-value is from a temporally successive pulse across an entire Y line, and then the next adjacent Y line is scanned (like the pattern of a progressive-scan TV scan pattern)). These adjacent scan patterns are advantageous where slight eye movement may be expected, since only very small incremental changes in height due to movement of the eye will occur between successive spots, and minor changes will occur between successive lines. However there can be artifacts caused be accumulated heat from large numbers of spots formed in a small area in a small amount of time.

Figure 3:
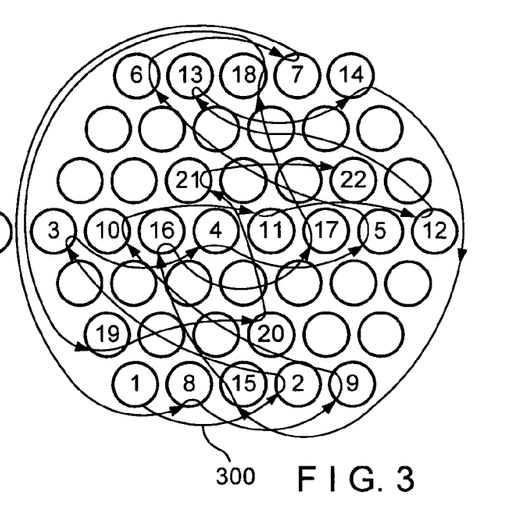
FIG. 3 is a plan view of a scan pattern 300 for an array of spots.

FIG. 3 is a plan view of a scan pattern 300 for an array of spots. Hopping scan pattern 300 forms spaced-apart spots with successive laser pulses, i.e., successive pulses are scanned to spaced-apart spot locations, both in the X and Y directions, and later pulses fill in the intermediate spots later in the operation. In the embodiment shown, reference numbers 1 through 22 again represent the temporal order in which the spots are formed. After forming spot 1 in the lower left, two spot locations are skipped, and spot 2 is formed in the third spot over, next to the lower right. Spot 3 is then formed at the left of the middle line, spot 4 near the middle, and spot 5 towards the right Note that each spot is moved to some minimal distance that is a multiple (>1) of the final spatial spot-to-spot spacing from the prior spot formed. In this example the spot 8 and spot 15 are located between spot 1 and spot 2, but are formed at a much later time (e.g., after spots 7 and 14, respectively, on the top line). In other embodiments, other spatial spacings for successive temporal pulses are used, for example, 10 spots, 20 spots, 50 spots, 100 spots, or other values. For ample, some embodiments use a 100-spot spacing on a Cartesian grid of say, 500 spots by 500 spots, wherein the $1^{st}$, $101^{st}$, $201^{st}$, $301^{st}$ and $401^{st}$ spot on line one are formed, then the $1^{st}$, $101^{st}$, $201^{st}$, $301^{st}$ and $401^{st}$ spot on line 101 are formed, then the $1^{st}$, $101^{st}$, $201^{st}$, $301^{st}$ and $401^{st}$ spot on line 201 are formed, and so on such that the minimum spatial distance between temporally successive spots is 100 times the final minimum spot-to-spot spacing The next pass forms the $2^{nd}$, $102^{nd}$, $202^{nd}$, $302^{nd}$ and $402^{nd}$ spot on line one, then the $2^{nd}$, $102^{nd}$, $202^{nd}$, $302^{nd}$ and $402^{nd}$ spot on line 101 are formed, and so on, until all 500 by 500 spots that form the desired cut are formed The present invention, which greatly speeds up e cutting process, makes such a spot-hopping process possible, since much less eye movement is possible with the shorter operation time, on the order of one to two seconds, or less, in some embodiments.

FIGS. 4A–6A and 4B–6B represent a LASIK-like procedure.

Figure 4A:
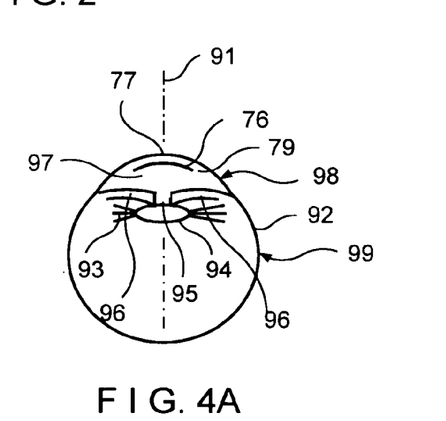
FIG. 4A is a side cross-section view of an eye 99 after a flap cut 77.
Figure 4B:
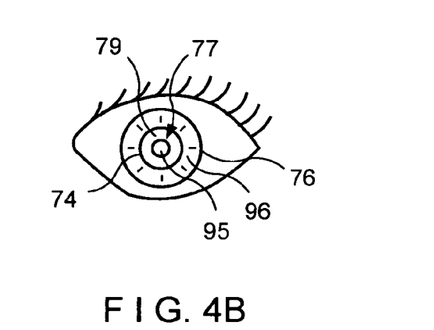
FIG. 4B is a front view of the eye 99 of FIG. 4A.

FIG. 4A is a side cross-section view of an eye 99 after a flap cut 77. FIG. 4B is a front view of the eye 99 of FIG. 4A. Eye 99 includes sclera 92, cornea 98, stroma 97, iris 96, pupil 95, lens 94 and lens muscle 93, and has an optical axis 91. A cut 77 is e.g., parallel to the corneal surface, and is extended to the surface with a cut 76 that extends in a partial arc (e.g., in some embodiments, a 270-degree to 315-degree arc centered on the optical axis) leaving a binge 74. In some embodiments, a fiducial mad 76 is formed, e.g., as a small subsurface cut on both flap 75 and the surrounding corneal tissue, in order that the flap can be realigned for a better fit when later replaced to its attached configuration.

Figure 5A:
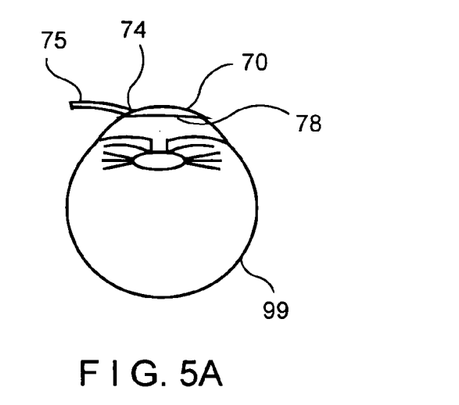
FIG. 5A is a side cross-section view of an eye 99 after a posterior lenticule cut 78.
Figure 5B:
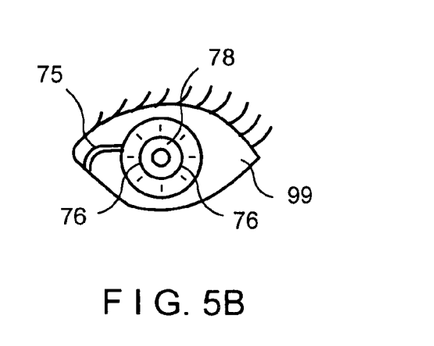
FIG. 5B is a front view of the eye 99 of FIG. 5A.

FIG. 5A is a side cross-section view of an eye 99 after a posterior lenticule cut 78. FIG. 51 is a front view of the eye 99 of FIG. 5A. Flap 75 has been folded back in some embodiments, traditional excimer laser sculpting is performed in the LASIK manner that ablates the surface of the exposed stroma. In other embodiments, a lenticule 70 is formed by an additional FSK cut 78. In some embodiments, cut 78 is formed before cut 77 of FIG. 4A (such as described in FIGS. 7A and 7B but with a flap rather than a slit cut to the surface). In some embodiments, lenticule 70 is mechanically removed (e.g., grabbed with tweezes, or flushed with a saline stream from a small jet).

Figure 6A:
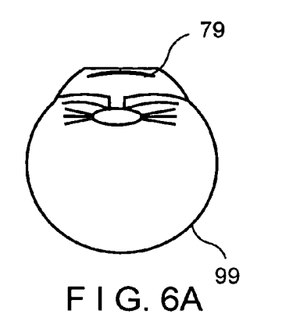
FIG. 6A is a side cross-section view of an eye 99 after the flap has been reseated.
Figure 6B:
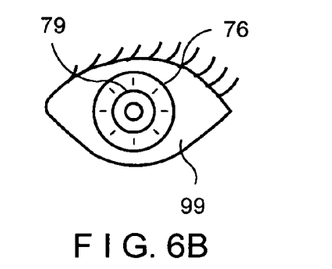
FIG. 6B is a front view of the eye 99 of FIG. 6A.

FIG. 6A is a side cross-section view of an eye 99 after the flap has been reseated FIG. 6B is a front view of the eye 99 of FIG. 6A. With lenticule 70 removed, the surface of cornea 98 above the surgery area is altered to correct die visual focus and improve vision.

Figure 7A:
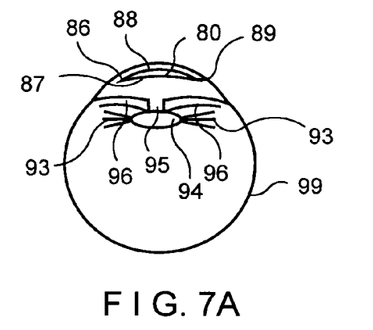
FIG. 7A is a side cross-section view of an eye 99 after two lenticule cuts.
Figure 7B:
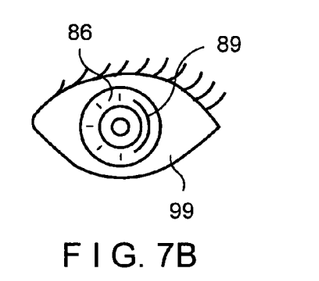
FIG. 7B is a front view of the eye 99 of FIG. 7A.

FIGS. 7A–9A and 7B–9B represent an FLK procedure,

FIG. 7A is a side cross-section view of an eye 99 after two lenticule, cuts. FIG. 7B is a front view of the eye 99 of FIG. 7A. In the embodiment shown, a posterior surface cut 87 is made and an anterior surface cut 88 is made, defining lenticule 80 having a circumference 86. In some embodiments, an access slit 89 is made through the surface of the cornea and connecting to lenticule 80.

Figure 8A:
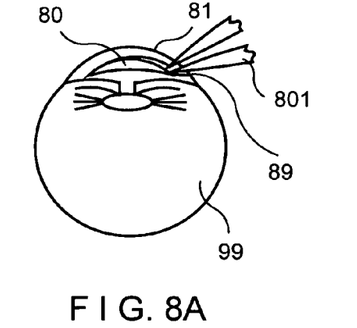
FIG. 8A is a side cross-section view of an eye 99 as lenticule 80 is removed.
Figure 8B:
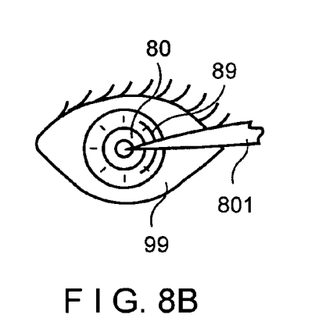
FIG. 8B is a front view of the eye 99 of FIG. 8A.

FIG. 8A is a side cross-section view of an eye 99 as lenticule 80 is removed FIG. 8B is a front view of the eye 99 of FIG. 8A. In some embodiments, lenticule 80 is mechanically removed (e.g. grabbed with tweezers 801, or flushed with a saline steam from a small jet).

Figure 9A:
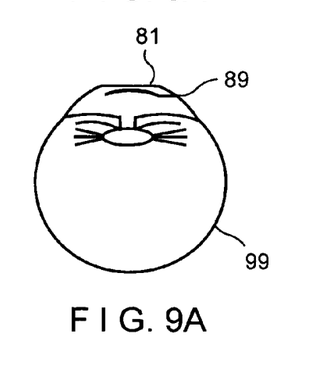
FIG. 9A is a side cross-section view of an eye 99 after the cornea surface layer has been reseated.
Figure 9B:
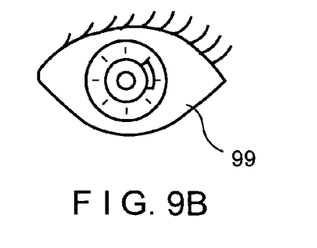
FIG. 9B is a front view of the eye 99 of FIG. 9A.

FIG. 9A is a side cross-section view of an eye 99 after the cornea surface has been reseated. FIG. 9B is a front view of the eye 99 of FIG. 9A. With lenticule 80 removed, the surface of cornea 98 above the surgery area is altered to correct the visual focus and improve vision.

FIG. 10 is a side cross-section view of eye interface 1000 with eye 99, showing more details of a typical eye-stabilization and optical interface device 133 of FIG. 1 used in some embodiments. The anatomical structure of eye 99, as described above in the description for FIG. 1, includes cornea 98 anterior to the pupil 95, the iris 96, and the sclera 92. Optical axis 91 of eye 99 passes through the cornea 98. Cornea 98 includes five tissue layers including the epithelium 981, Bowman's membrane 982, stroma 983, Decemet's membrane 984, and endothelium 985. In some embodiments, suction ring 1016, on the end of support 1014, is placed against sclera 92 and a small vacuum is formed through piping 1015 to chamber 1017 to hold the eye 99 in a fixed location. In some embodiments, actuator 1012 moves disposable contact lens 1010 into contact with the anterior surface of cornea 98 in some embodiments, the index of refraction of contact lens 1010 is made to match the index of refraction of cornea 98, in order that only anterior surface 1011 of lens 1010 changes the direction or focus of beam 129. This allows computer 135 of FIG. 1 to control scanner 132 in a manner that is more easily calculated, since only the shape of anterior surface 1011 of contact lens 1010 changes the light direction. In some embodiments, the refraction of the eye is checked both before and with contact lens 1010 in place by focusing light on various locations across the entire retina, in order to obtain the amount and type of correction needed, and thus to calculate the size and shape of lenticule 80 that will be cut. In some embodiments, scanned laser beam 129 moves the beam 129 such that temporally successive pulses are focused to spaced-apart spot locations (e.g., spatial spots 1, 2, 3, 4, 5, 6, 7, 8, and 9 on cut 87 at the posterior lenticule surface are more than the minimum final spot-to-spot spacing, as are later formed spatial spots 11, 12, 13, 14, 15, 16, 17, 18, and 19 on cut 88 at the anterior surface of lenticule 80). In some embodiments, once the cuts are complete (e.g., in one to two seconds or less), contact lens 1010 is withdrawn, and lenticule 80 is mechanically removed through access slit 89. In some embodiments, slit 89 includes an interlocking configuration, such that unless forced by some threshold amount of force, it will not open, in order to improve the post-operative healing process.

Repetition Rate

Rather than using a low repetition rate laser (e.g., few kHz), the present invention uses a laser system 110 that runs at a repetition rate between about 50 kHz and 1 MHz or greater. In some embodiments, the pulse rate is adjustable by design. In some embodiments, the laser system 110 is combined with a Zeiss optical scanning system 130, and the laser section's pulse-repetition rate is set at 200 kHz. In some embodiments, the power out of laser system 110 is lower than that used in lower-repetition-rate lasers (in some embodiments, the pulse energy leaving laser system 110 is two microJoules), but this is sufficient for the application. The high repetition rate and high scan rate means that the cutting can occur much more rapidly. This is important because the longer the cutting tin, he longer the eye must be maintained stationary (or be tracked which is also difficult). For low-repetition-rate lasers to shorten the cutting time, they need to cut larger areas at once (bigger spot size). They can do this because they have higher pulse energy than laser system 110, but it results in a coarser cut, and with more acoustic shock and heat damage that does not heal as well and does not provide as accurate a refractive correction. Therefore system 100 producing many small spots very quickly is a superior method to producing fewer large spots in a similar timeframe.

Note that the high repetition rate laser system 110 is only useable because optical scanning system 130 (in some embodiments, made by Zeiss) has a very fast scanner that can raster the beam across the eye fast enough to place spots in the desired pattern at 200 kHz.

Because the laser can be turned on and off rapidly and precisely (using downcounter 115, e.g., under the control of computer 135) and the scanner 132 can be moved rapidly, this enables the user to define unique raster patterns on the eye (such as spaced-apart spots from temporally successive pulses), not achievable with other system. For example, a pattern in which each successive pulse is focused to a second spot at a distance from a respective previous first spot, and at a later time pulses are focused to other spots between the first and second spot. These patterns may be used to reduce thermal damage by not cutting in adjacent spots in consecutive exposures, or may enable the creation of unique eye correction patterns by allowing shaping of the cornea in new ways.

Pro-compression

Femtosecond pulses are distorted (due to dispersion) as they go trough optical fibers, lenses, or other elements along an optical path (e.g., in scanning system 130). Therefore, the pulse of light available for cutting at the eye 99 will not be the sane as the pulse that comes out of the laser stem due to dispersion from the complex optical system between these two points. Since it is desirable, in some embodiments, to have a pulse of about 350 fs at the eye 99, we need to produce a pulse (of stream 127) back at the exit of laser system 110 that, after going through all of the optics, will have this duration at the focal point in the eye. This is achieved by precompression of the pulse at, e.g., the last stage (preconditioning grating compressor 117) of the laser system 99. In other embodiments, the preconditioning is performed earlier, and accommodates later stages within laser system 110. Instead of the normal grating compressor that would be used to produce a 350-fs pulse at the output of the laser, a compressor is used that adds a second-order dispersion to the pulse that exactly compensates for the second-order dispersion of the optical system leading to the eye. In some embodiments using the Zeiss scanning system 130, this precompression is $-2 \times 10^4$ fs$^{-2}$.

It should also be noted that the optical energy is also dissipated throughout the system, so that while at the laser the pulse energy is 2 µJ, when it reaches the eye, it will be significantly lower (in some embodiments, on the order of 1 µJ or less). This cutting energy is also important to the overall process. Too little energy does not cut because the threshold for LIOB is not achieved, while too much energy can cause thermal damage to adjacent tissue or larger spots.

Some embodiments of the present invention provide an apparatus that includes a pulsed laser 110 having a pulse repetition rate of more than 50,000 pulses per second and a per-pulse length of less than one picosecond, and an optical path including a scanning head operably coupled to receive laser light from the pulsed laser and operable to scan an output light pattern suitable to sculpt tissue for a surgical procedure using at least 100000 pulses in less than ten seconds. In some embodiments, the pulsed laser 110 includes one or more sections of fiber-optic gain medium.

In some embodiments, the surgical procedure is a complete surface cut of an ophthalmologic surgical procedure, the cut defining a surface, at least a portion of which is within a corneal stroma.

In some embodiments, the surgical procedure uses at least 500000 pulses in less than five seconds.

In some embodiments, the surgical procedure uses at least 500000 pulses in less than four seconds.

In some embodiments, the surgical procedure uses at least 500000 pulses in less than three seconds.

In some embodiments, the surgical procedure uses at least 500000 pulses in less an two seconds.

In some embodiments, the surgical procedure uses at least 500000 pulses in one second or less.

In some embodiments, the surgical procedure uses at least 500000 pulses in one-half second or less.

In some embodiments, the surgical procedure uses at least 500000 pulses in one-quarter second or less.

In some embodiments, the surgical procedure uses at least 400000 pulses in less than five seconds.

In some embodiments, the surgical procedure uses at least 400000 pulses in less than four seconds.

In some embodiments, the surgical procedure uses at least 400000 pulses in less than three seconds.

In some embodiments, the surgical procedure uses at least 400000 pulses in less than two seconds.

In some embodiments, the surgical procedure uses at least 400000 pulses in less than one second.

In some embodiments, the surgical procedure uses at least 300000 pulses in less than five seconds.

In some embodiments, the surgical procedure uses at least 300000 pulses in less than four seconds.

In some embodiments, the surgical procedure uses at least 300000 pulses in less than three seconds.

In some embodiments, the surgical procedure uses at least 300000 pulses in less than two seconds.

In some embodiments, the surgical procedure uses at least 300000 pulses in less than one second.

In some embodiments, the surgical procedure uses at least 200000 pulses in less than five seconds.

In some embodiments, the surgical procedure uses at least 200000 pulses in less than four seconds.

In some embodiments, the surgical procedure uses at least 200000 pulses in less than three seconds.

In some embodiments, the surgical procedure uses at least 200000 pulses in less than two seconds.

In some embodiments, the surgical procedure uses at least 200000 pulses in less than one second.

In some embodiments, the surgical procedure uses at least 100000 pulses in less than five seconds.

In some embodiments, the surgical procedure uses at least 100000 pulses in less than four seconds.

In some embodiments, the surgical procedure uses at least 100000 pulses in less than three seconds.

In some embodiments, the surgical procedure uses at least 100000 pulses in less than two seconds.

In some embodiments, the surgical procedure uses at least 100000 pulses in less than one second.

In some embodiments, the surgical procedure uses at least 100000 pulses in one-half second or less.

In some embodiments, the surgical procedure uses at least 50000 pulses in less than five seconds.

In some embodiments, the surgical procedure uses at least 50000 pulses in less than four seconds.

In some embodiments, the surgical procedure uses at least 50000 pulses in less than three seconds.

In some embodiments, the surgical procedure uses at least 50000 pulses in less than two seconds.

In some embodiments, the surgical procedure uses at least 50000 pulses in less than one second.

In some embodiments, the surgical procedure uses at least 50000 pulses in one-half second or less.

In some embodiments, the surgical procedure uses at least 25,000 pulses in one-quarter second or less.

In some embodiments, the surgical procedure uses at least 50000 pulses in one-quarter second or less.

In some embodiments, the surgical procedure uses at least 100000 pulses in one-quarter second or less.

In some embodiments, the surgical procedure forms a first cut that defines a posterior surface of a lenticule within a corneal stroma, a second cut that defines a lenticule anterior surface of the lenticule, and a slit cut that extends to the cornea surface, wherein the three cuts are completed within five seconds. In some such embodiments, the slit cut either forms or subtends an arc of less than 180 degrees measured from the lenticule's center.

In some embodiments, the surgical procedure firms a first cut that defines a posterior surface of a corneal flap that can be folded back to expose a stroma surface to allow a conventional LASIK operation on the exposed stroma surface, wherein the first cut is completed within two seconds.

Some embodiments further include a precompressor that creates a negative dispersion in each pulse that compensates for a dispersion of the optical path after the precompressor.

In some embodiments, the scanning head focuses at least 100000 pulses per second and the per-pulse length is less than 999 femtoseconds.

In some embodiments, the scanning head focuses at least 100000 pulses per second and the per-pulse length is less than 750 femtoseconds.

In some embodiments, the scanning head focuses at least 100000 pulses per second and the per-pulse length is less than 500 femtoseconds.

In some embodiments, the scanning head focuses at least 100000 pulses per second and the per-pulse length is less than 400 femtoseconds.

In some embodiments, the scanning head focuses at least 100000 pulses per second and the per-pulse length is 350 femtoseconds or less.

In some embodiments, the scanning head focuses at least 200000 pulses per second and the per-pulse length is less than 999 femtoseconds.

In some embodiments, the scanning head focuses at least 200000 pulses per second and the per-pulse length is less than 750 femtoseconds.

In some embodiments, the scanning head focuses at least 200000 pulses per second and the per-pulse length is less than 500 femtoseconds.

In some embodiments, the scanning head focuses at least 200000 pulses per second and the per-pulse length is less than 400 femtoseconds.

In some embodiments, the scanning head focuses at least 200000 pulses per second and the per-pulse length is 350 femtoseconds or less.

In some embodiments, the scanning head focuses at 200000 pulses per second and the per-pulse length is 350 femtoseconds.

In some embodiments, the scanning head focuses at 200000 pulses per second and the per-pulse length is about 500 femtoseconds.

In some embodiments, the scanning head focuses at 200000 pulses per second and the per-pulse length is about 450 femtoseconds.

In some embodiments, the scanning head focuses at 200000 pulses per second and the per-pulse length is about 400 femtoseconds.

In some embodiments, the scanning head focuses at 200000 pulses per second and the per-pulse length is about 350 femtoseconds.

In some embodiments, the scanning head focuses at 200000 pulses per second and the per-pulse length is about 300 femtoseconds.

In some embodiments, the scanning head focuses at 200000 pulses per second and the per-pulse length is about 250 femtoseconds.

In some embodiments, the scanning head focuses at 200000 pulses per second and the per-pulse length is about 200 femtoseconds.

In some embodiments, the scanning head focuses at 200000 pulses per second and the per-pulse length is about 150 femtoseconds.

In some embodiments, the scanning head focuses at 200000 pulses per second and the per-pulse length is about 100 femtoseconds.

In some embodiments, the scanning head focuses at 200000 pulses per second and the per-pulse length is about 50 femtoseconds.

In some embodiments, the scanning head focuses at least 500000 pulses per second and the per-pulse length is less than 999 femtoseconds.

In some embodiments, the scanning head focuses at least 500000 pulses per second and the per-pulse length is less than 750 femtoseconds.

In some embodiments, the scanning head focuses at least 500000 pulses per second and the per-pulse length is less than 500 femtoseconds.

In some embodiments, the scanning head focuses at least 500000 pulses per second and the per-pulse length is less than 400 femtoseconds.

In some embodiments, the scanning head focuses at least 500000 pulses per second and the per-pulse length is 350 femtoseconds or less.

In some embodiments, the scanning head focuses at least 1000000 pulses per second and the per-pulse length is less than 999 femtoseconds.

In some embodiments, the scanning head focuses at least 1000000 pulses per second and the per-pulse length is less Man 750 femtoseconds.

In some embodiments, the scanning head focuses at least 1000000 pulses per second and the per-pulse length is less than 500 femtoseconds.

In some embodiments, the scanning head focuses at least 1000000 pulses per second and the per-pulse length is less than 400 femtoseconds In some embodiments, the scanning head focuses at least 1000000 pulses per second and the per-pulse length is 350 femtoseconds or less.

Other embodiments of the invention include a method that includes generating a stream of pulses having a pulse repetition rate of at least about 50000 pulses per second and a per-pulse length of less than one picosecond, and scanning and focusing the stream to an output light pattern suitable to sculpt tissue for a surgical procedure using at least 100000 pulses in less than ten seconds. In some embodiments, the stream of pulses is generated by a pulsed laser that includes one or more sections of fiber-optic gain medium.

In some embodiments of the method, the surgical procedure is a complete surface out of an ophthalmologic surgical procedure, the cut defining a surface, at least a portion of which is within a corneal stroma.

In some embodiments of the method, the Scanning and focusing uses at least 200000 pulses to form at least one cut that is completed in less than five seconds.

In some embodiments of the method, the scanning and focusing uses at least 200000 pulses to form at least one cut that is completed in less than two seconds.

In some embodiments of the method, the scanning and focusing forms a first cut that defines a posterior surface of a lenticule within a corneal stroma, a second cut that defines a lenticule anterior surface of the lenticule, and a slit cut that extends to the cornea surface, wherein the three cuts are completed within five seconds. In some such embodiments, the slit cat either forms or subtends an arc of less than 180 degrees measured from the lenticule's center.

In some embodiments of the method, the surgical procedure forms a first cut that defines a posterior surface of a corneal flap that can be folded back to expose a stroma surface to allow a LASIK operation on the exposed stroma surface, wherein the first cut is completed within two seconds.

Some embodiments of the method further include precompressing each pulse to create a negative dispersion that compensates for a dispersion of an optical path after the precompressor.

In some embodiments of the method, tie scanning and focusing focuses at least 100000 pulses per second and the per-pulse length is less than 500 femtoseconds.

In some embodiments of the method, the scanning and focusing focuses at least about 200000 pulses per second and the per-pulse length is less than 400 femtoseconds.

In some embodiments of the method, the scanning and focusing focuses at 200000 pulses per second and the per-pulse length is 350 femtoseconds.

In some embodiments of the method, the scanning and focusing focuses at about 200000 pulses per second and the per-pulse length is about 350 femtoseconds.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. An apparatus comprising:
    a pulsed laser that includes a fiber optical gain medium and having a pulse repetition rate of more than 50000 pulses per second and a per-pulse length of less than one picosecond;
    an optical path including a scanning head operably coupled to receive laser light from the pulsed laser and operable to scan an output light pattern suitable to sculpt tissue for a surgical procedure using at least 100000 pulses in less than ten seconds; and
    a precomperssor that creates a negative dispersion in each pulse that compensates for a dispersion of the optical path after the precompressor.

2. The apparatus of claim 1, wherein the surgical procedure is a complete surface cut of an ophthalmologic surgical procedure, the cut defining a surface, at least a portion of which is within a corneal stroma.

3. The apparatus of claim 1, wherein the surgical procedure uses at least 200000 pulses in less than five seconds.

4. The apparatus of claim 1, wherein the surgical procedure uses at least 200000 pulses in less than two seconds.

5. The apparatus of claim 1, wherein the surgical procedure forms a first cut that defines a posterior surface of a lenticule within a corneal stroma, a second cut that defines a lenticule anterior surface of the lenticule, and a slit cut that extends to the cornea surface, wherein the three cuts are completed within five seconds.

6. The apparatus of claim 5, wherein the slit cut either forms or subtends an arc of less than 180 degrees measured from the lenticule's center.

7. The apparatus of claim 1, wherein the surgical procedure forms a first cut that defines a posterior surface of a corneal flap that can be folded back to expose a stroma surface to allow a conventional LASIK operation on the exposed stroma surface, wherein the first cut is completed within two seconds.

8. The apparatus of claim 1, wherein the scanning bead focuses at least 100000 pulses per second and the per-pulse length is less than 500 femtoseconds.

9. The apparatus of claim 1, wherein the scanning head focuses at least about 200000 pulses per second and the per-pulse length is less than 400 femtoseconds.

10. A method comprising:
    generating a stream of optical pulses having a pulse repetition rate of at least about 50000 pulses per second and a per-pulse length of less than one picosecond using an optical fiber gain medium;
    scanning and focusing the stream to an Output light pattern suitable to sculpt tissue for a surgical procedure using at least 100000 pulses in less than ten seconds providing a precompressor; and
    precompressing each pulse to create a negative dispersion that compensates for a dispersion of an optical path after the precompressor.

11. The method of claim 10, wherein the surgical procedure is a complete surface cut of an ophthalmologic surgical procedure, the cut defining a surface, at least a portion of which is within a corneal stroma.

12. The method of claim 10, wherein the scanning and focusing uses at least 200000 pulses to form at least one cut that is completed in less than five seconds.

13. The method of claim 10, wherein the scanning and focusing uses at least 200000 pulses to form at least one cut that is completed in less than two seconds.

14. The method of claim 10, wherein the scanning and focusing forms a first cut that defines a posterior surface of a lenticule within a corneal stroma, a second cut that defines an lenticule anterior surface of the lenticule, and a slit cut that extends to the cornea surface, wherein the tree cuts are completed within five seconds.

15. The method of claim 14, wherein the slit cut either forms or subtends an arc of less than 180 degrees measured from the lenticule's center.

16. The method of claim 10, wherein the surgical procedure forms a first cut that defines a posterior surface of a corneal flap that can be folded back to expose a stroma surface to allow a LASIK operation on the exposed stroma surface, wherein the first cut is completed within two seconds.

17. The method of claim 10, wherein the scanning and focusing focuses at least 100000 pulses per second and the per-pulse length is less than 500 femtoseconds.

18. The method of claim 10, wherein the scanning and focusing focuses at least about 200000 pulses per second and the per-pulse length is less than 400 femtoseconds.

19. An apparatus comprising:
    optical fiber means for generating a stream of pulses having a pulse repetition rate of at least about 50000 pulses per second and a per-pulse length of less than one picosecond;
    means for scanning and focusing the stream to an output light pattern suitable to sculpt tissue for a surgical procedure using at least 100000 pulses in less than ten seconds; and
    means for Precompressing each pulse to create a negative dispersion that compensates for a dispersion of an optical path after the precompressor.

20. The apparatus of claim 19, wherein the means for scanning and focusing is operable to form a complete cut for an ophthalmologic surgical procedure, the cut defining a surface, at least a portion of which is within a corneal stroma.

21. The apparatus of claim 19, wherein the scanning and focusing uses at least 200000 pulses to form at least one cut that is completed in less than five seconds.

22. The apparatus of claim 19, wherein the scanning and focusing uses at least 200000 pulses to form at least one cut that is completed in less than two seconds.

23. The apparatus of claim 19, wherein the means for scanning and focusing is operable to form a first cut that defines a posterior surface of a lenticule within a corneal stroma, a second cut that defines an lenticule anterior surface of the lenticule, and a slit cut that extends to the cornea surface, wherein the tree cuts are completed within five seconds.

24. The apparatus of claim 23, wherein the slit cut either forms or subtends an arc of less than 180 degrees measured from the lenticule's center.

25. The apparatus of claim 19, wherein the surgical procedure forms a first cut that defines a posterior surface of a corneal flap that can be folded back to expose a stroma surface to allow a LASIK operation on the exposed stroma surface, wherein the first cut is completed within two seconds.

26. The apparatus of claim 19, wherein the means for scanning and focusing focuses at least 100000 pulses per second and the per-pulse length is less than 500 femtoseconds.

27. The apparatus of claim 19, wherein the means for scanning and focusing focuses at least about 200000 pulses per second and the per-pulse length is less than 400 femtoseconds.

28. An apparatus comprising:
a pulse laser comprising a fiber optical amplifier and having a per-pulse length of less than one picosecond;
an optical path including a scanning head operably coupled to receive laser light from the pulsed laser and operable to scan an output light pattern suitable to sculpt tissue for a surgical procedure; and
a precompressor that creates a negative dispersion in each pulse that compensates for a dispersion of the optical path after the precompressor.

29. The apparatus of claim 28, wherein the surgical procedure is a complete surface cut of an ophthalmologic surgical procedure, the cut defining a surface, at least a portion of which is within a corneal stroma.

30. The apparatus of claim 28, wherein the surgical procedure uses at least 200000 pulses in less than five seconds.

31. The apparatus of claim 28, wherein the surgical procedure uses at least 200000 pulses in less than two seconds.

32. The apparatus of claim 28, wherein the surgical procedure forms a first cut that defines a posterior surface of a lenticule within a corneal stroma, a second cut that defines a lenticule anterior surface of the lenticule, and a slit cut that extends to the cornea surface, wherein the three cuts are completed within five seconds.

33. The apparatus of claim 32, wherein the slit cut either forms or subtends an arc of less than 180 degrees measured from the lenticule's center.

34. The apparatus of claim 28, wherein the surgical procedure forms a first cut that defines a posterior surface of a corneal flap that can be folded back to expose a stroma surface to allow a conventional LASIK operation on the exposed stroma surface, wherein the first cut is completed within two seconds.

35. The apparatus of claim 28, wherein the scamming head focuses at least 100000 pulses per second and the per-pulse length is less than 500 femtoseconds.

36. The apparatus of claim 28, wherein the scanning head focuses at least about 200000 pulses per second and the per-pulse length is less than 400 femtoseconds.

* * * * *